United States Patent [19]

Crawford et al.

[11] Patent Number: 5,229,274

[45] Date of Patent: Jul. 20, 1993

[54] GENE ENCODING ONE STEP CEPHALOSPORIN C AMIDASE AND EXPRESSION THEREOF IN RECOMBINANT BACILLUS

[75] Inventors: Mark S. Crawford, Bothell; David B. Finkelstein; John A. Rambosek, both of Seattle, all of Wash.

[73] Assignee: Merck & Co., Inc., Rahway, N.J.

[21] Appl. No.: 819,717

[22] Filed: Jan. 13, 1992

Related U.S. Application Data

[62] Division of Ser. No. 372,399, Jun. 27, 1989, Pat. No. 5,104,800.

[51] Int. Cl.$^5$ ............... C12N 15/55; C12N 15/31; C12N 9/80
[52] U.S. Cl. ............... 435/69.1; 435/172.3; 435/228; 435/320.1; 536/23.2; 536/24.1
[58] Field of Search ............... 435/51, 69.1, 172.3, 435/228, 320.1; 536/27

[56] References Cited

U.S. PATENT DOCUMENTS

| | | | |
|---|---|---|---|
| 3,144,395 | 8/1964 | Murao | 435/51 |
| 3,239,394 | 3/1966 | Walton et al. | 435/50 |
| 3,522,250 | 7/1970 | Kerwin et al. | 435/50 |
| 3,749,641 | 7/1973 | Takahashi et al. | 435/50 |
| 3,801,458 | 4/1974 | Fildes et al. | 435/47 |
| 3,821,081 | 6/1974 | Abe et al. | 435/51 |
| 3,880,713 | 4/1975 | Fleming et al. | 435/51 |
| 3,915,798 | 10/1975 | Yamaguchi et al. | 435/51 |
| 3,930,949 | 1/1976 | Kutzbach et al. | 435/51 |
| 3,945,888 | 3/1976 | Takahashi et al. | 435/50 |
| 3,960,662 | 6/1976 | Matsuda et al. | 435/51 |
| 3,962,036 | 6/1976 | Liersch et al. | 435/51 |
| 4,141,790 | 2/1979 | Niwa et al. | 435/51 |
| 4,774,179 | 9/1988 | Ichikawa et al. | 435/51 |
| 4,981,789 | 1/1991 | Lein | 435/51 |

FOREIGN PATENT DOCUMENTS

| | | |
|---|---|---|
| 780676 | 9/1972 | Belgium . |
| 321849 | 6/1984 | European Pat. Off. . |
| 0275901A2 | 7/1988 | European Pat. Off. . |
| 3447023 | 6/1986 | Fed. Rep. of Germany . |
| 2241557 | 4/1975 | France . |
| 50-107186 | 2/1975 | Japan . |
| 52-082791 | 2/1977 | Japan . |
| 52-143289 | 6/1977 | Japan . |
| 52-128293 | 10/1977 | Japan . |
| 53-86094 | 3/1978 | Japan . |
| 53-94093 | 8/1978 | Japan . |
| 54-110394 | 8/1979 | Japan . |
| 58-190399 | 5/1983 | Japan . |
| 60-110292 | 6/1985 | Japan . |
| 61-21097 | 1/1986 | Japan . |
| 61-152286 | 7/1986 | Japan . |
| 63-74488 | 8/1988 | Japan . |
| 2142336A | 1/1985 | United Kingdom . |

OTHER PUBLICATIONS

Dev. Ind. Microbiol., 5, 349 (1964).
Agric. Biol. Chem. 45, 1561–67 (1981).
Process Biochem., 11, 21 (1976).
DNA 3: 479–488 (1984).
DNA 5: 219–225 (1986).
J. Mol. Biol. 186, 547–555 (1985).
Gene 29: 21–26 (1984).
Molec. Gen. Genet. 168, 111–115 (1979).
J. Bact. 142, 508–512 (1980).
Journal of Bacteriology, Dec. 1987, pp. 5815–5820.
Journal of Bacteriology, Sep. 1985, pp. 1222–1228.
Applied and Environmental Microbiology, Nov. 1988, pp. 2603–2607, vol. 54, No. 11.
Matsuda et al., *J. Bact* 169: 5821–5826, Dec. 1987.

*Primary Examiner*—Robert A. Wax
*Assistant Examiner*—Stephen Walsh
*Attorney, Agent, or Firm*—Raymond M. Speer; Charles M. Caruso

[57] ABSTRACT

A process for the one-step conversion of cephalosporin C and derivatives thereof to the corresponding 7-aminocephalosporanic acid and derivatives comprising treating said cephalosporin C and derivatives with a cephalosporin C amidase enzyme of a recited sequence, the DNA encoding said enzyme, and expression thereof in a suitable host, e.g., Bacillus species under the control of a suitable promoter.

3 Claims, No Drawings

1

GENE ENCODING ONE STEP CEPHALOSPORIN C AMIDASE AND EXPRESSION THEREOF IN RECOMBINANT BACILLUS

This is a division of application Ser. No. 07/372,399, filed Jun. 27, 1989, now U.S. Pat. No. 5,104,800.

BRIEF SUMMARY OF THE INVENTION

The present invention relates to an improved process for the one-step conversion of cephalosporin C and derivatives thereof to the corresponding 7-aminocephalosporanic acid (7-ACA) and derivatives comprising treating said cephalosporin C and derivatives with a cephalosporin C amidase enzyme of a recited sequence, the DNA encoding said enzyme, and expression thereof in suitable host, e.g., Bacillus species under the control of a suitable promoter.

The present invention further relates to an enzyme, cephalosporin C amidase, having the specific amino acid sequence and physical/chemical characteristics set forth further below, as well as to any subunit thereof which is enzymatically active as a one-step cephalosporin C amidase.

The present invention still further relates to the DNA fragment encoding an enzyme, cephalosporin C amidase, having the nucleotide base sequence capable of expressing said enzyme, set forth further below.

The present invention also relates to expression of the DNA fragment, i.e., the gene encoding an enzyme, cephalosporin C amidase, in any suitable prokaryotic or eukaryotic host, especially in species of the the genus Bacillus, more especially in *Bacillus megaterium* and *Bacillus subtilis*. This is accomplished, as explained in more detail further below, by cloning the gene coding for cephalosporin C amidase activity from a particular strain of *B. megaterium*, fusing it to a promoter sequence, e.g., a strong constitutive promoter, and transforming the resulting construction into the desired host, e.g., *B. subtilis* and *B. megaterium*, which are maintained in an appropriate culture medium. Cephalosporin C amidase activity is monitored and harvesting of the enzyme is carried out by conventional means.

BACKGROUND OF THE INVENTION

The present invention is in the field of enzymatic cleavage (deacylation), especially one-step cleavage of the 7-aminoadipolyl side chain (also referred to as 7-α-aminoadipyl) of cephalosporin C. Since the 7-aminoadipolyl side chain is removed by cleavage of an amide linkage, the particular enzyme which accomplishes the conversion is referred to herein as an amidase. Cephalosporin C itself is a fermentation product which is the starting point for nearly all currently marketed cephalosporins. However, synthetic manipulation to produce these various commercial cephalosporins basically starts with the 7-aminocephalosporanic acid, which must be derived from the cephalosporin C by cleavage of the 7-aminoadipolyl side chain.

Currently, the method of choice in the art for cleaving the 7-aminoadipoyl side chain is chemical. The basic imino-halide process requires blocking of the amino and carboxyl groups on the 7-aminoadipolyl side chain, and several methods for accomplishing this are currently used. However, as presently employed, the chemical cleavage process has serious disadvantages. Among these are the requirements of a multi-step and complex process, extremely low operating temperatures, expensive reagents, significant quantities of process by-products resulting in effluent treatment problems, and purification of a highly impure starting material before chemical treatment beings. Consequently, there has been an ongoing search for a microbiological or fermentative process which would achieve enzymatic deacylation of cephalosporin C to provide 7-aminocephalosporanic acid on a more economic basis than the chemical process currently in use.

However, this search for a successful microbiological process has largely proved futile, certainly with respect to one of commercial scale. This is a result of the particular characteristics of the aminoadipoly side chain of the cephalosporin C molecule, since, by contrast, penicillin G, which has a phenylacetyl side chain, has been successfully deacylated by enzymatic cleavage using penicillin acylase produced by a variety of microorganisms. Reports of successful one-step enzymatic deacylation of cephalosporin C in the literature, on the other hand, are often unreproducible or provide only very marginal yields.

Moreover, no person to date has succeeded in isolating and sequencing an enzyme from the genus Bacillus, cephalosporin C amidase, which can achieve one-step cleavage of the aminoadipoly side chain of cephalosporin C. Nor, has anyone isolated and sequenced the gene which encodes the cephalosporin C amidase enzyme, or succeeded in expressing that gene in a prokaryotic host.

A summary of the literature which describes these ongoing efforts to achieve enzymatic cleavage of cephalosporin C is set out below.

| | |
|---|---|
| 1. One-Step Enzymatic Deacylation: | |
| Ceph C → 7-ACA | |
| Dev. Ind. Microbial., 5, 349 (1964) | |
| U.S. Pat. No. 3,239,394 | |
| (Merck) | |
| Soil enrichment method | Achromobacter, |
| of screening and selecting | Brevibacterium |
| for microorganisms | Flavobacterium |
| Jap. Pat. Pub. 53-94093 (1978) | |
| (Meiji) Pseudomonas sp. BN-188 | |
| Jap. Pat. Pub. 52-143289 (1977) | Aspergillus sp. |
| U.S. Pat. No. 4,141,790 | Alternaria sp. |
| (Meiji) | |
| U.S. Pat. No. 4,774,179 (1988) | Pseudomonas sp. |
| Jap. Pat. Pub. 61-21097 (1986) | SE-83 and |
| (Asahi) | SE-495 |
| Fr. Pat. 2,241,557 (1975) | Bacillus cereus |
| (Aries) | var. fluorescens |
| Jap. Pat. Pub. 52-082791 (1977) | Bacillus |
| (Toyo Jozo) NRRL B 5385 | megaterium |
| N-(N'-phenylthiocarbamyl)- | |
| cephalosporin C 7-ACA | |
| Ger. Pat. 3,447,023 (1986) | Bacillus |
| (Hoechst) | licheniformis |
| In the presence of a-keto | |
| acids; enzyme is D-amino acid | |
| transaminase | |
| 2. One-Step Enzymatic Deacylation: | |
| Penicillin G → 6-APA | |
| Jap. Pat. Pub. 58-190399 (1983) | Bacillus |
| (Shionogi) | megaterium |
| var. penicilliticum | |
| ATCC 14945 | |
| U.S. Pat. No. 3,144,395 (1964) | Bacillus |
| (Olin Mathieson) | megaterium |
| Br. Pat. Pub. 2,142,336A (1985) | Bacillus |
| (Squibb) | megaterium |
| 3. Two-Step Enzymatic Deacylation: | |
| Ceph C → 7-ACA | |
| U.S. Pat. No. 3,960,662 (1976) | |
| Agric. Biol. Chem. 45, 1561–67 (1981) | |
| (Toyo Jozo) | |
| Deamination with D-amino | Pseudomonos sp. |

| -continued | |
|---|---|
| acid oxidase followed by deacylation EP-A- 0 275 901-A2 (1988) (Hoechst) | |
| i) Ceph C GL-7-ACA* [U.S. Pat. No. 3,801,458 (1974) (Glaxo)] | Trigonopsis variabilis |
| ii) GL-7-ACA* 7-ACA gamma-glutamyl-transpeptidase | Pseudomonas Anthrobacter parafineus Bacillus subtilis |
| 4. Enzymatic Deacylation: GL-7-ACA* → 7-ACA Jap. Pat. Pub. 52-128293 (1977) 53-86094 (1978) (Banyu) | Bacillus, Arthrobacter, Alcaligenes |
| 5. Enzymatic Deacylation: Other → 7-ACA a) Phenoxy- and Phenylacetyl 7-ADCA 7-ADCA U.S. Pat. No. 3,821,081 (1974) | Bacillus megaterium |
| Process Biochem., 11, 21 (1976) (Toyo Jozo) U.S. Pat. No. 3,749,641 (1973) (Takeda) U.S. Pat. No. 3,915,798 (1975) Belg. Pat. No. 780,676 (Toyo Jozo) | 61 different genera Anthrobacter simplex Kluyvera citrophila Proteus rettgeri Bacillus megaterium |
| b) Phenoxy-7-ADCA → 7-ADCA U.S. Pat. No. 3,880,713 (1975) (Glaxo) | Erwinia aroideae |
| c) Cephalothin → 7-ACA U.S. Pat. No. 3,522,250 (1970) (American Home Products) | Escherichia coli |
| d) Various cephalosporins → 7-ACA U.S. Pat. No. 3,930,949 (1976) (Bayer) penicillin acylase | E. coli |
| U.S. Pat. No. 3,962,036 (1976) (Ciba-Geigy) 3-lower alkoxy-7-acyl cephalosporins; microorganisms possessing acylase activity | E. coli, Bacillus megaterium, subtilis, Micrococcus roseus lysodeikticus Alcaligenes faecalis, Aerobacter cloacae, Fusarium avenaceum, semitectum, Emericellopsis minima, Pennicillium chrysogenum, Aspergillus ochraceus, Trichophyton mentagrophytes, Epidermophyton floccosum Streptomyces lavendulae |
| Jap. Pat. Pub. 50-107186 (1975) (Toyo Brewing) phenylacetamido 7-ACA derivatives are deacylated | Arthrobacter, Bacillus, Escherichia, Kluyvera, Micrococcus, Nocardia, Proteus, Xanthomonas, |
| 6. Enzymatic Acylation: 7-ACA → Other | |

| -continued | |
|---|---|
| U.S. Pat. No. 3,945,888 (1976) (Takeda) 7-ACA → cephalosporins Jap. Pat. Pub. 54-110394 (Banyu) | E. coli, Bacillus, Proteus, Pseudomonas |
| 7-ACA → cephapirin | Arthrobacter viscosus |
| 7. One-Step/Two Enzyme Deacylation: Ceph C → 7-ACA Jap. Pat. Pub. 63 74,488 (1988) (Asahi) Recombinant E. coli expression of D-amino acid oxidase and GL-7-ACA* acylase construct | Trigonopsis variabilis, Comamonas |

*GL-7-ACA = glutaryl 7-ACA = 3-acetoxymethyl-7-beta-(4-carboxybutanamido)ceph-3-em-4-carboxylic acid

DETAILED DESCRIPTION OF THE INVENTION

In accordance with the present invention there is provided a process for the one-step conversion of cephalsoporin C and derivatives thereof of the formula:

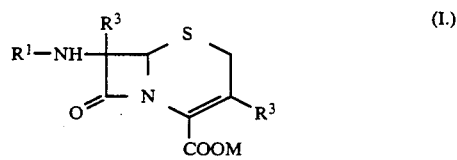

where $R^1$ is $HO_2C-CH(CH_2)_3CO-$;
$\phantom{R^1 \text{ is } HO_2C-} \overset{|}{NH_2}$

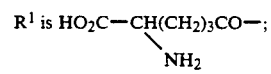

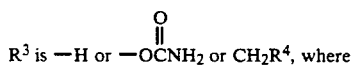

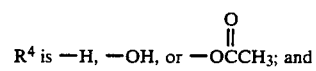

—; —H; alkali metal or other pharmaceutically acceptable salt; pharmaceutically acceptable ester; or readily removable carboxyl covering group;
to a 7-aminocephalosporanic acid of the formula:

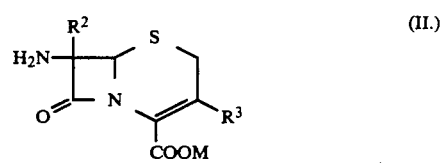

where $R^2$, $R^3$, and M are as defined above;

COMPRISING treating a compound of Formula I with an enzyme, cephalosporin C amidase, capable of converting a compound of Formula I to a compound of Formula II in one step; said enzyme comprising the following primary translation product amino acid sequence or a post-translational modification thereof:

```
  1 MKFIKSFILV TFSFFCMITP AFASVPGVDK SMGRGATKGI VSVSHPLAAE AGIKILKQGG

61 NAVDAAAAIQ LSLNVVEPMM SGIGGGGFIM IYNKKENKIT MLDSREMAPQ NVTPELFLDG

121 KGKPIPFSKR HTTGKAVGVP GTLKGVETAL EKYGTLDISQ VIDPAIKQAE KGVKVNWITA

181 QYIDENVKKL QNNQAAANVF VPNGQPLKEG DTLVQPDLAK TLKLIKKQGS EVFYSGQIGK

241 ALTKEVQKRE GTMTTEDLEN YVVKEREPIR SEYRGYELAG AASPSSGSLT VQQILELMEG

301 FDVQKMGANS PEYLHYLTEA MHLAFADRAA YMADEDFYDV PTKGLLDEDY IKERRKIINP

361 NRSTADVKEG DPWKYEGTEP TSMKKVKEEK TPIGQTTHFS VMDKWGNMVA YTTTIEQVFG

421 SGIMVPDYGF MLNNEMTDFD ATPGGVNQVE PGKRPRSSMS PTFVLKDGNP FMAIGSPGGA

481 TIIASVSETI MNVLDHQMLI QDAILAPRIY SAGYPTVRWE PGIEQNTRLE LMGKGHVYEE

541 KPQHIGNVQA VIFDYEKGKM YGGADNTREG TVQGVYNVST KSKKPKEIKE EKKGPFTLKV

601 NGAVYPYTEA QMKLINEKPY IQSDKLLLGL GVIGTGDLET FRPDKKSYLP VIKVAKSLGY

661 KAKWNEKDKE ALLEKDPADI EDPEDDGSVT IIFHSKFKFH MVDNTLRDEE FEVIVVLTLN

721 EC
``` wherein, for the above sequence, the following amino acid abbreviations are employed:
Ala=A; Arg=R; Asn=N; Asp=D; Cys=C; Gln=Q; Glu=E; Gly=G; His=H; Ile=I; Leu=L; Lys=K; Met=M; Phe=F; Pro=P; Ser=S; Thr=T; Trp=W; Try=Y; Val=V.

In accordance with the present invention, there is also provided an enzyme, cephalosporin C amidase, capable of one-step cleavage of the aminoadipoly side chain of cephalosporin C to give 7-ACA, and having the primary translation product amino acid sequence recited in the paragraph immediately above and any post-translational modifications thereof, and having the physical/chemical characteristics described in detail further below.

In accordance with the present invention there is further provided the purified, isolated and sequenced DNA fragment, i.e., the gene encoding an enzyme, cephalosporin C amidase, having the amino acid sequence recited in the paragraph further above. The nucleotide base sequence of the gene is set out further below, as are the nucleotide bases of the regulatory sequences which precede and follow the sequence of the gene itself. This gene was isolated from a particular strain of Bacillus megaterium which was found to have cephalosporin C amidase activity in accordance with assays described further below.

In accordance with the present invention there is still further provided a method of expressing the cephalosporin C amidase enzyme having the amino acid sequence set out further above in a suitable prokaryotic or eukaryotic host, e.g., Bacillus species by fusing the gene sequence encoding the enzyme to a promoter sequence, e.g., a strong constitutive promoter sequence, cloning the resulting construction into an appropriate vector, and transforming said vector into said suitable host. Details of this method are set out further below.

Vectors containing the construction of fused gene and 141/142 promoter sequences described further below, transformed into a Bacillus megaterium and a B. subtilis host, have been deposited with the American Type Culture Collection (ATCC), 12301 Parklawn Drive, Rockville, Md. 20852, and have been assigned deposit numbers 68024 and 68023, respectively.

The One-Step Enzymatic Cleavage Process

With reference to the compounds of Formula I above, the group $R^1$ defines the moiety

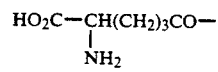

which is the cephalosporin C 7-aminoadipoyl side chain.

For the group "M", the expression "readily removable carboxyl covering group" means a conventional substituent which takes the place of the hydrogen of the carboxyl group and thereby prevents said group from reacting with any reagents employed in any subsequent synthesis. Such covering of the carboxyl group is often necessary to prevent unwanted competing reactions involving said groups from taking place. The conventional covering substituent must also be "removable", by which is meant that it is selectively removable, i.e., it is not likely to be removed during the course of ordinary procedures which are to be carried out on the cephalosporin nucleus and side chains, while, on the other hand, it is likely to be removed by procedures which are not so harsh as to disturb the basic ring structure of the cephalosporin nucleus or unprotected substituents thereon.

It will also be noted that for M=H in Formula II, at physiological pH an internal zwitterion is formed by the groups $NH_3^+$ and $COO^-$, so that M, in that case, is actually $-$, indicating an anion.

The group $R^3$ is defined to include various substituents characteristic of typical fermentation products, e.g., for cephalosporin C, $R^3$ would be $CH_2R^4$ where $R^4$ is

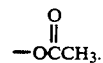

It is contemplated that none of the substituents defining $R_3$ would in any way interfere with the enzymatic action of the cephalosporin C amidase of the present invention, largely for the reasons discussed above.

The group $R^3$ is defined to include various substituents characteristic of typical fermentation products, e.g., for cephalosporin C, R³ would be CH₂R⁴ where R⁴ is

It is contemplated that none of the substituents defining R₃ would in any way interfere with the enzymatic action of the cephalosporin C amidease of the present invention, largely for the reasons discussed above.

Thus, in accordance with the method of the present invention, desacetoxycephalosporin C (R³=CH₂R⁴ where R⁴=H) may be converted to 7-aminodesacetoxycephalosporanic acid (7-ADCA) to an extent essentially equivalent to the conversion of cephalosporin C to 7-aminocephalosporanic acid (7-ACA). This results from the fact that the functional group at the 3-position is not crucial to the binding to substrate to the enzyme.

the process of one-step enzymatic conversion of cephalosporin C and derivatives to 7-aminocephalosporanic acid and derivatives with which the present invention is concerned may be schematically represented as follows:

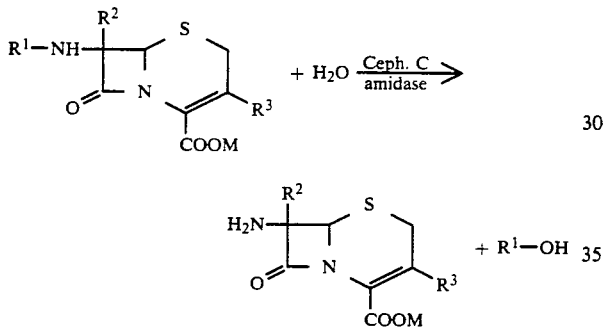

More particularly, the conversion of cephalosporin C to 7-aminocephalosporanic acid may be illustrated as follows:

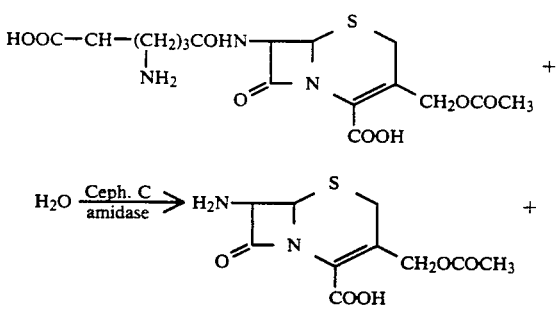

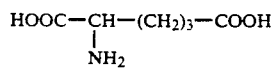

The process of the present invention may be carried out in any way which effectively brings the cephalosporin C amidase of the present invention into contact with the compounds of Formula I so that enzymatic conversion of these compounds to the compounds of Formula II can take place. This is the definition of the term "treating" in its broadest context. Ordinarily, it would be preferred to employ a cell free broth of crude cephalosporin C or derivative as the feed stream and treat it in a batch-wise fashion with crude cephalosporin C amidase broth. This approach realizes the greatest efficiencies since it does not require any substantial purification of the reactants initially. Of course, modifications are possible. E.g., the reactants may be purified to whatever extent desired before being brought into contact with each other. Also, it would be possible to carry out the process in a continuous manner rather than batch-wise. The contacting of the reactants thereselves may be modified in various ways in keeping with advances in process technology. Thus, an immobilized enzyme column may be employed for the cephalosporin C amidase with the compound of Formula I being passed through the column. Another example of such process technology is that relating the membrane reactors. The preferred method of contacting the reactants is by way of the immobilized enzyme column.

Further below working examples describe the method currently employed to demonstrate the enzymatic deacylation of cephalosporin C, which involves a preliminary purification of the cephalosporin C amidase, largely for the purpose of increasing the concentration of enzyme and thus promoting the production of higher amounts of 7-aminocephalosporanic acid. Consequently, the method in the working examples, would be necessarily be suggestive of methods which would be utilized for commercial production.

The Cephalosporin C Amidase Enzyme

The primary translation product, or precursor, which gives rise to the cephalosporin C amidase enzyme of the present invention comprises 722 amino acids, beginning with methionine (Met) and ending with cysteine (Cys), the sequence for which is set out further above. The primary translation product is processed, i.e., modified by the producing host, to yield an active enzyme consisting essentially of two subunits, the beginning amino acid sequences of which are underlined in the overall sequence as follows:

```
  1 MKFIKSFILV TFSFFCMITP AFASVPGVDK SMGRGATKGI VSVSHPLAAE AGIKILKQGG

61 NAVDAAAAIQ LSLNVVEPMM SGIGGGGFIM IYNKKENKIT MLDSREMAPQ NVTPELFLDG

121 KGKPIPFSKR HTTGKAVGVP GTLKGVETAL EKYGTLDISQ VIDPAIKQAE KGVKVNWITA

181 QYIDENVKKL QNNQAAANVF VPNGQPLKEG DTLVQPDLAK TLKLIKKQGS EVFYSGQIGK

241 ALTKEVQKRE GTMTTEDLEN YVVKEREPIR SEYRGYELAG AASPSSGSLT VQQILELMEG

301 FDVQKMGANS PEYLHYLTEA MHLAFADRAA YMADEDFYDV PTKGLLDEDY IKERRKIINP

361 NRSTADVKEG DPWKYEGTEP TSMKKVKEEK TPIGQTTHFS VMDKWGNMVA YTTTIEQVFG
```

```
421 SGIMVPDYGF MLNNEMTDFD ATPGGVNQVE PGKRPRSSMS PTFVLKDGNP FMAIGSPGGA

481 TIIASVSETI MNVLDHQMLI QDAILAPRIY SAGYPTVRWE PGIEQNTRLE LMGKGHVYEE

541 KPQHIGNVQA VIFDYEKGKM YGGADNTREG TVQGVYNVST KSKKPKEIKE EKKGPFTLKV

601 NGAVYPYTEA QMKLINEKPY IQSDKLLLGL GVIGTGDLET FRPDKKSYLP VIKVAKSLGY

661 KAKWNEKDKE ALLEKDPADI EDPEDDGSVT IIFHSKFKFH MVDNTLRDEE FEVIVVLTLN

721 EC
```

The gene product, i.e., the primary translation product comprising 722 amino acids, is a part of the present invention to the extent that it is enzymatically active as described herein. Also, as noted above, enzymatically active subunits thereof, particularly post-translational modifications which inherently result in enzymatic activity, are included. Other, artificial changes are also possible. Predictably, smaller subunits of the cephalosporin C amidase enzyme of the present invention, or different conformations of that same enzyme, will retain the full enzymatic activity of the enzyme whose sequence is recited herein. These forms of the amidase enzyme of the present invention are the full functional equivalents thereof and are thus contemplated to be a part of the present invention. These forms are sometimes referred to as microheterogeneous forms, since they are a single gene product, i.e., a protein produced from a single gene unit of DNA, which is structurally modified following translation. It is possible, using techniques well known to a biochemist, to effect various changes in the cephalosporin C amidase enzyme of the present invention, and then evaluate its enzymatic activity as a cephalosporin C amidase quickly and efficiently using the assays described further below. Such well-known techniques include acetylation at the N-terminus, glycosylation, phosphorylation, and proteolysis. Proteolysis may include exoproteolysis wherein one or more terminal amino acids are sequentially, enzymatically cleaved to produce microheterogeneous forms which have fewer amino acids then the original gene product. Proteolysis may also include endoproteolytic modification that results from the action of endoproteases which cleave the peptide at specific locations within the amino acid sequence. Similar modifications can occur during the purification process which may result in the production of microheterogeneous forms. The most common modification occurring during purification is proteolysis, which is, however, generally held to a minimum by the use of protease inhibitors.

As is well known, the biochemical action of an enzyme is determined not only by its amino acid sequence, but by its overall conformation as well. Moreover, the conformation of an enzyme is subject to environmentally induced changes, e.g., by pH, temperature, solvent systems, culture media, ionic factors, and the like. To the extend that such environmentally induced conformational changes in the the enzyme do not result in loss of cephalosporin C amidase activity, the various conformations of the enzyme are a part of the present invention.

The amino acid sequence of the cephalosporin C amidase enzyme of the present invention, recited further above, was deduced by DNA sequence analysis of the gene coding for the enzyme, and the accuracy of the results have been verified by sequencing three independent isolates from three different strains of *Bacillus megaterium*. However, since 100% accuracy cannot be totally assured, it has been considered desirable to also identify the cephalosporin C amidase enzyme of the present invention in terms of a number of physical and chemical attributes which it uniquely has. Purification of the enzyme for which such data has been derived is explained in more detail further below. Those data are set out in the following table:

A. Structural
 1. Apparent MW: 126,000 by gel filtration
 2. Subunit MW (by SDS PAGE): Alpha (large): 45 kd; Beta (small): 37 kd
 3. Stoichiometry: alpha (2) beta (2) oligomer (MW approximately 165 kd)
 4. Specific activity: 1–3 μmol 7-ACA/mg enzyme/hr (increases as enzyme is diluted)

B. Kinetic
 1. Temperature optimum: 37°–40° C.
 2. pH optimum: 7–8
 3. Stable pH range: 5.0–8.0
 4. Activity stimulated by 10–15% (w/v) ammonium sulfate
 5. Km: 1.3 mM cephalosporin C amidase [Km with glutaryl-4-aminobenzoate (GAB) approximately M but with 20-fold higher turnover number]
 6. Substrate specificity:
  DAC>Ceph C>DAOC
  12.5% 9.1% 2.3% (% 7-ACA production at 3 h)
  [DAC=desacetylcephlosporin C; DAOC=desacetoxycephalosporin C]

C. Inhibitors
 1. NOT inhibited by PenG or 6-APA
 2. Potent inhibitors (>90% inhibition at 10 mM):

| Glycine | L-alanine |
| Glutamate | D-alanine |
| Glutamine | |

The Gene Encoding the Enzyme

The gene encoding the primary translation product cephalosporin C amidase enzyme of the present invention contains 722 codons, which correspond to the 722 amino acids of the primary translation product enzyme. The precise sequence of codons is set forth further below and for the gene itself begins with nucleotide base 1 and ends with base 2166, in the numbering system employed to set forth the sequence. The sequence of nucleotide bases (codons) which precede the gene sequence, bases −163 through −1, and the sequence of bases (codons) which follow the gene sequence, nucleotide bases 2167 through 2370, contain regulatory sequences of the gene within the *Bacillus megaterium* cell from which the gene was isolated. The preceding sequence contains, for example, a promoter sequence and a ribosome binding site. While these additional sequences are not a part of the gene itself, they are, nevertheless, a part of the present invention, since they potentially play a role in efficient transcription of the gene in the prokaryotic host Bacillus species. The entire sequence of nucleotide bases is shown in compact form in the following table:

```
-163 ATAGTAGAGA GTACATCACG CACATTCCAT
     CTGGTAATAG TGAAGTAGTC GAATCCTGTA
-103 ACAGCCCTTT GTGAATTTGT GAAGATCAGT
     AAAAGTTTCA TTAGTTATTG CATTTGTTTT
 -43 TAGAAACAAT GGATCTATAA TCATTTTGAA
     AGGAGACTAA TTTATGAAAT TTATAAAAAG
  18 TTTTATTTTA GTTACTTTCA GTTTCTTTTG
     TATGATTACA CCGGCTTTTG CAAGTGTCCC
  78 TGGAGTGGAT AAGTCAATGG GAAGGGGAGC
     AACCAAAGGA ATCGTATCAG TTTCTCATCC
 138 GTTAGCTGCT GAGGCAGGTA TAAAAATATT
     AAAACAAGGT GGAAATGCAG TCGATGCAGC
 198 AGCTGCCATT CAATTATCGT TAAATGTAGT
     TGAGCCAATG ATGTCTGGAA TTGGCGGCGG
 258 TGGTTTTATC ATGATTTATA ATAAAAGGA
     AAATAAAATA ACGATGCTCG ATAGCCGCGA
 318 AATGGCCCCG CAAAATGTAA CGCCTGAACT
     TTTTTTAGAT GGAAAAGGAA AACCAATTCC
 378 TTTTAGTAAG CGTCACACTA CTGGAAAAGC
     AGTAGGAGTT CCAGGAACGT TAAAGGGTGT
 438 CGAAACAGCT CTTGAGAAAT ATGGAACGTT
     GGATATATCT CAAGTAATAG ATCCAGCAAT
 498 TAAACAAGCA GAAAAGGGG TTAAAGTCAA
     TTGGATCACT GCTCAATATA TCGATGAAAA
 558 TGTAAAAAAA CTTCAAAATA ATCAAGCTGC
     AGCAAATGTG TTTGTTCCTA ACGGCCAACC
 618 CTTGAAAGAG GGAGATACCC TCGTTCAACC
     AGATCTGGCA AAGACGCTGA AATTAATTAA
 678 AAAACAAGGA TCGGAAGTAT TTTATAGTGG
     CCAAATTGGT AAAGCACTTA CCAAAGAAGT
 738 GCAAAAACGC GAAGGAACAA TGACAACAGA
     GGATTTAGAG AATTATGTGG TGAAAGAAAG
 798 AGAACCGATT AGATCGGAAT ATAGAGGATA
     CGAATTGGCA GGGGCAGCTT CACCAAGTTC
 858 AGGCAGCTTG ACTGTCCAAC AAATCCTAGA
     GCTAATGGAA GGATTCGATG TACAAAAGAT
 918 GGGGGCGAAC TCCCCTGAAT ATCTTCATTA
     TCTGACCGAA GCCATGCATC TAGCTTTTGC
 978 CGATCGCGCT GCCTATATGG CAGATGAAGA
```

-continued
```
     TTTTTATGAT GTACCAACAA AAGGACTATT
1038 GGATGAAGAT TATATAAAAG AAAGAAGAAA
     AATCATTAAT CCAAATAGAT CAACGGCTGA
1098 TGTAAAAGAA GGCGATCCAT GGAAGTATGA
     GGGCACAGAA CCCACTTCAA TGAAGAAGGT
1158 AAAAGAAGAG AAAACTCCGA TCGGACAAAC
     GACTCACTTT TCTGTCATGG ATAAGTGGGG
1218 AAATATGGTT GCTTATACGA CTACAATCGA
     GCAAGTATTC GGATCAGGTA TCATGGTACC
1278 TGATTATGGA TTCATGCTTA ATAATGAAAT
     GACGGATTTT GATGCGACTC CCGGTGGCGT
1338 TAACCAAGTA GAGCCAGGAA AAAGACCGAG
     AAGCAGTATG TCCCCGACCT TCGTATTAAA
1398 AGATGGTAAT CCCTTCATGG CCATTGGTTC
     ACCAGGCGGG GCGACGATAA TCGCATCGGT
1458 ATCTGAAACG ATTATGAATG TGCTTGACCA
     TCAAATGCTA ATTCAAGATG CGATACTTGC
1518 GCCACGTATT TATTCTGCTG GTTATCCGAC
     TGTTAGATGG GAACCGGGAA TTGAACAAAA
1578 TACAAGGTTG GAGTTAATGG GCAAAGGCCA
     TGTTTATGAA GAAAAACCCC AACATATCGG
1638 AAATGTGCAA GCTGTTATTT TTGATTATGA
     AAAGGGGAAA ATGTATGGAG GAGCCGACAA
1698 TACGAGAGAA GGAACTGTTC AAGGAGTGTA
     TAATGTATCC TATAAATCGA AAAAACCAAA
1758 AGAAATAAAA GAAGAAAAGA AGGGACCGTT
     TACCTTAAAA GTGAATGGAG CCGTTTATCC
1818 TTATACAGCT GAACAAATGA AACTGATAAA
     TGAAAAACCC TATATCCAAT CAGACAAATT
1878 GCTACTTGGT TTGGGTGTAA TTGGAACCGG
     GGACTTAGAA ACATTTAGAC CAGATAAAAA
1938 ATCGTACTTA CCGGTGATAA AAGTAGCGAA
     ATCATTAGGA TATAAAGCAA AATGGAACGA
1998 AAAAGATAAA GAGGCACTAT TGGAAAAAGA
     TCCGGCGGAT ATTGAAGATC CCGAAGATGA
2058 TGGTAGTGTT ACGATTATTT TTCACTCTAA
     GTTTAAGTTC CATATGGTTG ATAATACCCT
2118 GAGAGACGAA GAGTTTGAAG TGATAGTAGT
     CTTAACCCTA AATGAATGTT AATAATTCCC
2178 CTTTTGCTAT GTGCATAAGG GGCCAATTAT
     TTTTTTGGAA ATGATAGCTA AAAAGATTGG
2238 ACATTTTTCT ATGAAGCATT CGGTGCAAGG
```

```
              CTCATCTTAT ATCGCTGATA AACCCAGATA

2298 GTACTACCAA GCCAAAACCC ACCTGTGAAA

AAGTCCCCAA GGTTGTCACT TGGGAACTGT

2358 GCACCCAATC AAAA
```

In addition to the specific sequence of nucleotide bases set out above, the cephalosporin C amidase gene of the present invention is also uniquely characterized by the points at which various endonucleases, i.e., restriction enzymes, cut the gene. These are summarized in the following chart, where all of the enzymes shown have a recognition sequence six bases or more long:

```
            1        400        800       1200       1600       2000
         ----+----------+----------+----------+----------+----------+---------
Bal I    ----+----------+--------*--+----------+-----*----+----------+---------
Bgl I    ----+----------+----------+---*------+----------+----------+---------
Bgl II   ----+----------+------*---+----------+----------+----------+---------
Cla I    ----+----------+--*-------+----------+----------+----------+---------
Eco B    ----+----------+----------+----------+------*---+----------+---------
Eco B    ----+-----*----+----------+----------+----------+----------+---------
EcoP 15  ----+-----*----+----------+----------+----------+----------+---------
EcoP 15  ----+-*--------+----------+----------+------*---+----------+---------
Hpa I    ----+----------+----------+----------+---*------+----------+---------
Kpn I    ----+----------+----------+----------+*---------+----------+---------
Nco I    ----+----------+----------+-----*----+----------+----------+---------
Nde I    ----+----------+----------+----------+----------+----------+--*------
Nsi I    ----+----------+----------+----*-----+----------+----------+---------
Pst I    ----+----------+----*-----+----------+----------+----------+---------
Pvu I    ----+----------+----------+----*----*+----------+----------+---------
Pvu II   ----+-----*----+----------+----------+----------+----*-----+---------
Rru I    ----+----------+----------+----------+----------+----------+------*--
Rsh I    ----+----------+----------+-----*----*+----------+----------+---------
Sca I    ----+----------+----------+----------+----------+----------+------*--
Xmn I    ----+----------+----------+---*------+----------+----------+---------
Xor II   ----+----------+----------+----*----*+----------+----------+---------
```

The specific makeup of the nucleotide bases of the gene of the present invention, and corresponding amino acids of the enzyme of the present invention into which they are translated, are shown, on a percentage basis, in the following table:

| | | | | | | | | | | | |
|---|---|---|---|---|---|---|---|---|---|---|---|
| TTT Phe | 19 | 2.6% | TCT Ser | 7 | 1.0% | TAT Tyr | 25 | 3.5% | TGT Cys | 2 | .3% |
| TTC Phe | 8 | 1.1% | TCC Ser | 3 | .4% | TAC Tyr | 2 | .3% | TGC Cys | 0 | .0% |
| TTA Leu | 16 | 2.2% | TCA Ser | 10 | 1.4% | TAA — | 1 | — | TGA — | 0 | — |
| TTG Leu | 9 | 1.2% | TCG Ser | 6 | .8% | TAG — | 0 | — | TGG Trp | 5 | .7% |
| CTT Leu | 9 | 1.2% | CCT Pro | 7 | 1.0% | CAT His | 7 | 1.0% | CGT Arg | 2 | .3% |
| CTC Leu | 2 | .3% | CCC Pro | 7 | 1.0% | CAC His | 3 | .4% | CGC Arg | 3 | .4% |
| CTA Leu | 8 | 1.1% | CCA Pro | 14 | 1.9% | CAA Gln | 27 | 3.7% | CGA Arg | 0 | .0% |
| CTG Leu | 5 | .7% | CCG Pro | 12 | 1.7% | CAG Gln | 0 | .0% | CGG Arg | 0 | .0% |
| ATT Ile | 21 | 2.9% | ACT Thr | 12 | 1.7% | AAT Asn | 26 | 3.6% | AGT Ser | 8 | 1.1% |
| ATC Ile | 12 | 1.7% | ACC Thr | 9 | 1.2% | AAC Asn | 4 | .6% | AGC Ser | 3 | .4% |
| ATA Ile | 13 | 1.8% | ACA Thr | 11 | 1.5% | AAA Lys | 53 | 7.3% | AGA Arg | 12 | 1.7% |
| ATG Met | 27 | 3.7% | ACG Thr | 13 | 1.8% | AAG Lys | 15 | 2.1% | AGG Arg | 2 | .3% |
| GTT Val | 16 | 2.2% | GCT Ala | 15 | 2.1% | GAT Asp | 34 | 4.7% | GGT Gly | 14 | 1.9% |
| GTC Val | 7 | 1.0% | GCC Ala | 8 | 1.1% | GAC Asp | 5 | .7% | GGC Gly | 11 | 1.5% |
| GTA Val | 20 | 2.8% | GCA Ala | 19 | 2.6% | GAA Glu | 43 | 6.0% | GGA Gly | 33 | 4.6% |
| GTG Val | 11 | 1.5% | GCG Ala | 7 | 1.0% | GAG Glu | 14 | 1.9% | GGG Gly | 6 | .8% |

It is also an object of the present invention to provide a method of producing the cephalosporin C amidase enzyme in improved yields by expressing it in a suitable prokaryotic or eukaryotic host, e.g., a Bacillus species, where said host has been transformed with a construction resulting from fusing of said gene to a promoter sequence, e.g., a strong constitutive promoter. The elements of this process are described in detail immediately below.

Site-Specific In Vitro Mutagenesis

Transformation of the prokaryotic or eukaryotic host with a construction comprising the gene encoding the cephalosporin C amidase fused to a promoter sequence, e.g., a strong constitutive promoter sequence, requires use of a vector. Regarding the preferred prokaryotic host, a Bacillus species, in order to facilitate vector construction, a BamHI site was introduced in front of the amidase coding sequences by site-specific in vitro mutagenesis in which a thymine (T) residue 29 base pairs upstream from the start of translation was converted to a cytosine (C) residue. This was accomplished by synthesizing the following oligonucleotide:

5' AATGATTATGGATCCATTGT 3'

This oligonucleotide was hybridized to the cephalosporin C amidase gene cloned into M13mp19 and a standard mutagenesis reaction was carried out of the type described in DNA 3:479–488 (1984). Mutants incorporating the appropriate base change were identified by the presence of a new BamHI site and confirmed by DNA sequencing. The altered sequence and its position relative to the cephalosporin C amidase structural gene is indicated below:

```
              -20         -10          +1
               •           •            •
AAACAATGGATCCATAATCATTTTGAAAGGAGACTAATTT ATG AAA TTT
       BamHI                             Met Lys Phe
```

Synthesis of the Strong Constitutive Promoter

A synthetic promoter based on the HpaII promoter of pUB110, as described in DNA 5:219-225 (1986), was synthesized in the following manner: two oligonucleotides (141 and 142, respectively) with the following sequences were synthesized:

5'-GGGGGATCCACAGCCTCGCATATCACACACTTTATGAATATAAAGTAT-3'
[oligonucleotide 141]

5'-GGGGATCCAACCACTTCCAAGTAAAGTATAACACATATACTTTATATTC
ATA-3'
[oligonucleotide 142]

The two oligonucleotides are complementary through the last 16 base pairs of each oligonucleotide. They were thus hybridized to each other and filled in with DNA polymerase I Klenow fragment and a mixture of deoxynucleotides. This generated a double stranded structure suitable for cloning by virtue of the BamHI site present at the 5' end of each oligonucleotide.

Other promoters which are suitable for expression of the cephalosporin C amidase gene in a Bacillus prokaryotic host can be synthesized and are contemplated to be a part of the present invention. For example, the following promoter was synthesized and designated 90/91:

5'-GAATTCACTTAAAAATTTCAGTTGCTTAATCCTACAATTCTTGATATAATA
TTCTCATAGTTTGAAGGATCC-3'

This promoter has been reported in J. Mol. Biol., 186, 547-555 (1985) to be a strong Bacillus promoter and has been determined to be tenfold more active than the 141/142 promoter described above when driving expressions of the chloramphenicol acetyl transferase gene.

Yet another suitable promoter has been found which is a natural *Bacillus megaterium* promoter and was isolated therefrom. It was found to have about fivefold better activity than the 141/142 promoter in driving the expression of the chloramphenicol acetyl transferase gene. Its base pair sequence is as follows:

5'-GCTTCCTTCGCATTTCCGTTCATCATTAAATAGGGAGATAATCGCATTGTC
ATAATTAAATAGCTCCTTTGGTTCTATTJTTTTTAACCAAAATCTTTGAGT
ATCTTTCCAAGCTTCCTTTTTGAAACCTTGTCAGTGAATAAATAAACCACT
ATACCATTATTACCATGATTGTATTTTATAACAAGAACGTATGTTCGTCAA
TATATATCACTTGAAGACTAAACAATTTTCGATCCGGATTC-3'

Fusing of the Cephalosporin C Amidase Gene to the Synthetic Strong Constitutive Promoter The cephalosporin C amidase gene with the altered 5' sequence described above in the paragraph under "Site-Specific In Vitro Mutagenesis" and the synthetic strong constitutive promoter described in the paragraph immediately above were combined at the BamHI sites. A detailed description of this fusion product is shown in the paragraph immediately below, including the various promoter regions (A+T, −35, −10), the ribosome binding site (RBS), and the start of translation.

Construction of the Vector pCPC-1

The cephalosporin C amidase expression vector, labelled pCPC-1, was constructed by cloning the amidase gene fused to the strong constitutive promoter 141/142 into the *Bacillus/E. coli* shuttle vector pMK4 described in Gene 29:21-26 (1984).

```
         -100          -90          -80          -70          -60
           •            •            •            •            •
     GGA TCC ACA GCC TCG CAG AGC ACA CAC TTT ATG AAT ATA AAG TAT GTG
     BamHI           A + T Region          -35

-50          -40          -30          -20          -10
           •            •            •            •            •
     TTA TAC TTT ACT TGG AAG TGG TTG GGA TCC ATG GTC ATT TTG AAA GGA
                                    BamHI                       RBS
              141/142 Sequence              Gene Sequence 1           10           20           30
            •            •            •            •
     GAC TAA TTT ATG AAA TTT ATA AAA AGT TTT ATT TTA GTT ACT TTC AGT
                 Met Lys Phe Ile Lys Ser Phe Ile Leu Val Thr Phe Ser 40           50           60           70           80
            •            •            •            •            •
     TTC TTT TGT ATG ATT ACA CCG GCT TTT GCA AGT GTC CCT GGA GTG GAT
     Phe Phe Cys Met Ile Thr Pro Ala Phe Ala Ser Ala Pro Gly Val Asp
```

Expression of Cephalosporin C Amidase in *Bacillus subtilis* and *Bacillus megaterium*

The pCPC-1 vector described above was transformed into *B. subtilis* ATCC 39620 and *B. megaterium* NP-1 by standard methods, such as those described in Molec. Gen. Genet. 168, 111-115 (1979) and J. Bact. 142, 508-512 (1980). "NP-1" indicates a *B. megaterium* strain which produces little or no cephalosporin C amidase. Transformants and control cultures were grown overnight in LB media containing 10 μg/ml of chloramphenicol and used to inoculate cultures of fermentation media (FM) containing 10 μg/ml of chloramphenicol. These cultures were grown 3 to 4 days at 28° C. with shaking. Supernatants were concentrated 5 fold by ammonium sulfate precipitation (75% ammonium sulfate cut) and assayed for cephalosporin C amidase activity using cephalosporin C as substrate. The 200 μliter assay mixture contained 2 mg/ml cephalosporin C (final concentration) plus 180 μliters of 5× concentrated culture supernatant in 50 mM KHPO$_4$ (pH 7.5), 5% glycerol, and 15% NH$_4$SO$_4$. Liberation of 7-aminocephalosporanic acid (7-ACA) from cephalosporin C was assayed by HPLC.

*B. megaterium* NP-1 transformed with pCPC-1 liberated 157 μg of 7-ACA/ml of reaction mixture/3 hr assay time; whereas, control cultures of NP-1 liberated approximately 2 μg of 7-ACA. *B. subtilis* ATCC 39620 transformed with pCPC-1 liberated 0.52 μg of 7-ACA; whereas, control cultures of *B. subtilis* 39620 were negative.

Cephalosporin C amidase activity could also be detected in the overnight cultures grown in LB media when γ-glutamyl-p-aminobenzoic acid was used as the substrate for cephalosporin C amidase. *B. subtilis* 39620 transformed with pCPC-1 produced 2.7 units of activity (where 1 unit is defined as liberation of 1 nanomole of p-aminobenzoic acid (PABA)/minute/ml of culture supernatant); whereas, control cultures were negative. Using γ-glutamyl-p-aminobenzoic acid as substrate, the *B. megaterium* NP-1 transformed with pCPC-1 produced 3.5 units of amidase activity; whereas, control cultures were negative.

The Prokaryotic Host

As shown above, expression of the cephalosporin C amidase gene has been achieved in *Bacillus megaterium* and *Bacillus subtilis*. It is contemplated that, with use of a suitable promoter, expression of said gene can be obtained in any species of the Bacillus genus, and thus the present invention is directed to a method of expressing of said gene in a host comprising a member of the genus Bacillus.

It is also contemplated that with use of suitable promoter sequences and construction of suitable vectors containing constructs of the cephalosporin C amidase gene of the present invention fused to said promoter sequence, that it is possible to obtain expression of the gene in eukaryotic and other prokaryotic hosts, such as various species of Streptomyces, Saccharomyces, Aspergilus, Serratia, Cephalosporium, and Escherichia, among others.

In order to demonstrate the enzymatic deacylation of cephalosporin C to give 7-aminocephalosporanic acid (7-ACA), the general procedure illustrated below has been followed:

Enzyme preparation
Isolated colony from LB and chloramphenicol inoculate liquid LB media and chloramphenicol: 18 hours at 37° C.
inoculate production medium: 60-96 hours at 30° C.
harvest cell suspension and centrifuge to remove cells concentrate and partially purify activity by fractionation with (NH$_4$)$_2$SO$_4$ at 55-75% of saturation
Assay of activity: incubate 180 μl enzyme with 20 μl 20 mg/ml cephalosporin C; after 3 hours at 37° determine 7-ACA by HPLC assay A more detailed description of the manner in which the enzyme of the present invention has been isolated and purified is set out immediately below.

Enzyme Purification

Cultures of *B. megaterium* were grown as described. The cells were removed from the broth by centrifugation. The broth was brought to 55% saturation with respect to ammonium sulfate and the precipitate removed by centrifugation. The supernatant was then brought to 75% saturated with respect to ammonium sulfate and the cephalosporin C amidase containing precipitate pelleted by centrifugation. This pellet was resuspended in 1/10 of the original culture volume of 15% (w/v) ammonium sulfate, 50 mM sodium phosphate, 5% (w/v) glycerol pH 7.5.

The 10X concentrated enzyme was brought from 15% to 18% w/v ammonium sulfate by addition of saturated ammonium sulfate and filtered through a 0.4 micron filter. Four mls of this was injected onto a Synchrome Synchropak propyl column (25 cm×4.1 mM) which was previously equilibrated with 18% (w/v) ammonium sulfate, 50 mM potassium phosphate pH 7.0. The flow rate was 1 ml/min. For ten minutes after injection the mobile phase composition remained unchanged. From 10 to 40 minutes the mobile phase was changed in a linear gradient to 0% ammonium sulfate, 50 mM sodium phosphate pH 7. From 40-50 minutes the mobile phase composition remained unchanged. Two fractions/min. were collected and assayed for cephalosporin C amidase activity. The activity eluted from 22 to 25 minutes.

The five fractions with the most activity were pooled and concentrated by ultrafiltration in a Centricon 30 (Amicon) to about 50 μl. This concentrated enzyme was injected onto a Zorbox GF 250 (DuPont) column (250 mM×9.4 mM). The column had been equilibrated and was run in 10% (w/v) ammonium sulfate, 50 mM potassium phosphate pH 7.0 at 1 ml/min. Five fractions/min. were collected. All of the cephalosporin C amidase activity was recovered in two fractions at approximately 9 minutes after injection.

Sodium dodecyl sulfate gel electrophoresis of these active fractions showed the cephalosporin C amidase to be approximately 99% of the total coomasie stained protein.

As illustrated in more particular detail below, the general procedure described above were followed in the working examples:

EXAMPLE 1

Preparation and Assay of Cephalosporin C Amidase Activity from Cultures of *Bacillus megaterium*

Culture Conditions
1. The strains were maintained on LB agar plates (supplemented with 10 μg/ml chloramphenicol) of the following composition:

| COMPONENT | g/l |
|---|---|
| tryptone | 10 |
| yeast extract | 5 |
| NaCl | 5 |

-continued

| COMPONENT | g/l |
|---|---|
| agar | 15 |

2. Reisolated colonies were obtained by streaking on LB plus chloramphenicol plates followed by overnight incubation at 37° C. Isolated colonies were used to inoculate 5 ml of LB plus chloramphenicol liquid media, which is identical to the media listed above, except that it lacks the agar component. These culture were incubated overnight at 37° C.

3. The 5 ml overnight cultures were used to inoculate 40 ml cultures of fermentation media (FM) supplemented with 10 μg/ml chloramphenicol. FM is of the following composition:

| COMPONENT | g/l |
|---|---|
| beef extract | 4.5 |
| casitone | 9.0 |
| soybean meal | 15.0 |
| dextrose | 5.0 |
| soluble starch | 30 |
| lactose | 30 |

4. The cultures in FM were incubated at 30° C. on a rotary shaker (220 rpm) for 3-4 days, until the pH of the culture was 8.0 or above.

Enzyme Recovery

1. Cells were removed from the cultures by centrifugation at 10,000 rpm for 10 minutes.

2. To 2.5 ml of the above centrifuged supernatant was added 7.5 ml of saturated ammonium sulfate, followed by 10 minutes on ice and centrifugation at 10,000 rpm for 10 minutes. The pellets were resuspended in 0.5 ml of high salt buffer (HSB) for assay with cephalosporin C as substrate. HSB of the following composition:

| HSB |
|---|
| 50 mM KHPO$_4$, pH 7.5 |
| 5% glycerol |
| 15% NH$_4$SO$_4$ |

Enzyme Assay

1. The substrate stock solution was prepared by dissolving 20 mg of cephalosporin C in 1 ml of water.

2. Cephalosporin C stock solution (20 μl) was added to the recovered enzyme (180 μl) and the mixture was incubated at 37° C. for 3 hours. Formation of 7-ACA was monitored by HPLC. The following HPLC conditions were used:

| mobile phase | 50 mM KH$_2$PO$_4$ |
|---|---|
| flow rate | 2.0 ml/min |
| column | Waters Novapak C18, 0.4 × 10 cm |
| temperature | ambient |
| detector | 254 nm |
| sample size | 20 μl |
| instrument | Waters |

Retention time of the 7-ACA was ca. 5.0 minutes under these conditions.

Activity Assay Results

1. Following processing as described above, the enzyme preparation produced 157 μg of 7-ACA per ml of reaction mixture per 3 hour incubation in the presence of 2 mg/ml cephalosporin C.

EXAMPLE 2

One-step Enzymatic Conversion of Cephalosporin C to 7-Aminocephalosporanic Acid: Direct Measurement of the Cleavage Products In order to provide further evidence that the conversion of cephalosporin C to 7-aminocephalosporanic acid (7-ACA) in accordance with the present invention is indeed a one-step process accomplished by a single enzyme, (cephalosporin C amidase), cleavage is carried out as described above in Example 1; but in addition to measuring formation of 7-ACA by HPLC as described in Example 1, the appearance of the other cleavage product, aminoadipic acid, is measured as well. This is done using a Beckman 6300 High Performance Analyzer. The enzyme is incubated with cephalosporin C (2 mg/ml final concentration) for 2.8 hours at 37° C. The one to one molar ratio of isolated products is good evidence for a one-step conversion of cephalosporin C to 7-ACA by the amidase enzyme.

What is claimed is:

1. The isolated and purified DNA molecule encoding an enzyme, cephalosporin C amidase, capable of expressing said enzyme, and consisting essentially of the following nucleotide base sequence:

−163 ATAGTAGAGA GTACATCACG CACATTCCAT

CTGGTAATAG TGAAGTAGTC GAATCCTGTA

−103 ACAGCCCTTT GTGAATTTGT GAAGATCAGT

AAAAGTTTCA TTAGTTATTG CATTTGTTTT

−43 TAGAAACAAT GGATCTATAA TCATTTTGAA

AGGAGACTAA TTTATGAAAT TTATAAAAAG

18 TTTTATTTTA GTTACTTTCA GTTTCTTTTG

TATGATTACA CCGGCTTTTG CAAGTGTCCC

78 TGGAGTGGAT AAGTCAATGG GAAGGGGAGC

AACCAAAGGA ATCGTATCAG TTTCTCATCC

138 GTTAGCTGCT GAGGCAGGTA TAAAAATATT

AAAACAAGGT GGAAATGCAG TCGATGCAGC

198 AGCTGCCATT CAATTATCGT TAAATGTAGT

TGAGCCAATG ATGTCTGGAA TTGGCGGCGG

258 TGGTTTTATC ATGATTTATA ATAAAAAGGA

AAATAAAATA ACGATGCTCG ATAGCCGCGA

318 AATGGCCCCG CAAAATGTAA CGCCTGAACT

TTTTTTAGAT GGAAAAGGAA AACCAATTCC

378 TTTTAGTAAG CGTCACACTA CTGGAAAAGC

AGTAGGAGTT CCAGGAACGT TAAAGGGTGT

438 CGAAACAGCT CTTGAGAAAT ATGGAACGTT

GGATATATCT CAAGTAATAG ATCCAGCAAT

498 TAAACAAGCA GAAAAAGGGG TTAAAGTCAA

TTGGATCACT GCTCAATATA TCGATGAAAA

558 TGTAAAAAAA CTTCAAAATA ATCAAGCTGC

AGCAAATGTG TTTGTTCCTA ACGGCCAACC

-continued

```
 618 CTTGAAAGAG GGAGATACCC TCGTTCAACC
     AGATCTGGCA AAGACGCTGA AATTAATTAA
 678 AAAACAAGGA TCGGAAGTAT TTTATAGTGG
     CCAAATTGGT AAAGCACTTA CCAAAGAAGT
 738 GCAAAAACGC GAAGGAACAA TGACAACAGA
     GGATTTAGAG AATTATGTGG TGAAAGAAAG
 798 AGAACCGATT AGATCGGAAT ATAGAGGATA
     CGAATTGGCA GGGGCAGCTT CACCAAGTTC
 858 AGGCAGCTTG ACTGTCCAAC AAATCCTAGA
     GCTAATGGAA GGATTCGATG TACAAAAGAT
 918 GGGGGCGAAC TCCCCTGAAT ATCTTCATTA
     TCTGACCGAA GCCATGCATC TAGCTTTTGC
 978 CGATCGCGCT GCCTATATGG CAGATGAAGA
     TTTTTATGAT GTACCAACAA AAGGACTATT
1038 GGATGAAGAT TATATAAAAG AAAGAAGAAA
     AATCATTAAT CCAAATAGAT CAACGGCTGA
1098 TGTAAAAGAA GGCGATCCAT GGAAGTATGA
     GGGCACAGAA CCCACTTCAA TGAAGAAGGT
1158 AAAAGAAGAG AAAACTCCGA TCGGACAAAC
     GACTCACTTT TCTGTCATGG ATAAGTGGGG
1218 AAATATGGTT GCTTATACGA CTACAATCGA
     GCAAGTATTC GGATCAGGTA TCATGGTACC
1278 TGATTATGGA TTCATGCTTA ATAATGAAAT
     GACGGATTTT GATGCGACTC CCGGTGGCGT
1338 TAACCAAGTA GAGCCAGGAA AAAGACCGAG
     AAGCAGTATG TCCCCGACCT TCGTATTAAA
1398 AGATGGTAAT CCCTTCATGG CCATTGGTTC
     ACCAGGCGGG GCGACGATAA TCGCATCGGT
1458 ATCTGAAACG ATTATGAATG TGCTTGACCA
     TCAAATGCTA ATTCAAGATG CGATACTTGC
1518 GCCACGTATT TATTCTGCTG GTTATCCGAC
     TGTTAGATGG GAACCGGGAA TTGAACAAAA
1578 TACAAGGTTG GAGTTAATGG GCAAAGGCCA
     TGTTTATGAA GAAAAACCCC AACATATCGG
```

-continued

```
1638 AAATGTGCAA GCTGTTATTT TTGATTATGA
     AAAGGGGAAA ATGTATGGAG GAGCCGACAA
1698 TACGAGAGAA GGAACTGTTC AAGGAGTGTA
     TAATGTATCC TATAAATCGA AAAAACCAAA
1758 AGAAATAAAA GAAGAAAAGA AGGGACCGTT
     TACCTTAAAA GTGAATGGAG CCGTTTATCC
1818 TTATACAGCT GAACAAATGA AACTGATAAA
     TGAAAAACCC TATATCCAAT CAGACAAATT
1878 GCTACTTGGT TTGGGTGTAA TTGGAACCGG
     GGACTTAGAA ACATTTAGAC CAGATAAAAA
1938 ATCGTACTTA CCGGTGATAA AAGTAGCGAA
     ATCATTAGGA TATAAAGCAA AATGGAACGA
1998 AAAAGATAAA GAGGCACTAT TGGAAAAAGA
     TCCGGCGGAT ATTGAAGATC CGAAGATGA
2058 TGGTAGTGTT ACGATTATTT TTCACTCTAA
     GTTTAAGTTC CATATGGTTG ATAATACCCT
2118 GAGAGACGAA GAGTTTGAAG TGATAGTAGT
     CTTAACCCTA AATGAATGTT AATAATTCCC
2178 CTTTTGCTAT GTGCATAAGG GGCCAATTAT
     TTTTTTGGAA ATGATAGCTA AAAAGATTGG
2238 ACATTTTTCT ATGAAGCATT CGGTGCAAGG
     CTCATCTTAT ATCGCTGATA AACCCAGATA
2298 GTACTACCAA GCCAAAACCC ACCTGTGAAA
     AAGTCCCCAA GGTTGTCACT TGGGAACTGT
2358 GCACCCAATC AAAA
``` or any fragment thereof which will produce an enzyme which is enzymatically active as a one-step cephalosporin C amidase.

2. A recombinant DNA molecule comprising a portion having the nucleotide base sequence set out in claim 1, encoding a one-step cephalosporin C amidase enzyme, together with a promoter sequence suitable for expression of said amidase in a Bacillus prokaryotic host species.

3. A method for preparing an enzyme, cephalosporin C amidase, capable of one-step conversion of cephalosporin C to 7-ACA, consisting essentially of expression said enzyme in a Bacillus prokaryotic host species, where said host has been transformed with a vector containing a construction resulting from fusing a promoter sequence to a gene coding for said enzyme and having the nucleotide base sequence set out in claim 1.

* * * * *